United States Patent
Bublot et al.

(10) Patent No.: US 6,645,740 B1
(45) Date of Patent: Nov. 11, 2003

(54) NUCLEIC ACIDS ENCODINGS EQUINE GM-CSF

(75) Inventors: Michel Bublot, Delmar, NY (US); Jennifer Maria Perez, East Nassau, NY (US); Christine Michèle Pierrette Andreoni, Villette d'Anthon (FR)

(73) Assignees: Merial Limited, London (GB); Merial LLC, Duluth, GA (US)

( * ) Notice: Subject to any disclaimer, the term of this patent is extended or adjusted under 35 U.S.C. 154(b) by 0 days.

(21) Appl. No.: 09/589,460

(22) Filed: Jun. 7, 2000

Related U.S. Application Data

(60) Provisional application No. 60/138,843, filed on Jun. 10, 1999.

(51) Int. Cl.[7] .............................................. C12N 15/19
(52) U.S. Cl. ................. 435/69.5; 435/325; 435/252.3; 435/320.1; 536/23.5
(58) Field of Search ............................ 536/23.5, 23.4; 435/69.1, 69.5, 69.7, 325, 252.3, 320.1; 424/851, 192.1, 198.1

(56) References Cited

U.S. PATENT DOCUMENTS 5,162,111 A  *  11/1992  Grabstein et al.
5,980,911 A  *  11/1999  Corner et al.

FOREIGN PATENT DOCUMENTS

| WO | WO 92/05255 | 4/1992 |
|---|---|---|
| WO | WO 94/01133 | 1/1994 |
| WO | WO 98/03198 | 1/1998 |

OTHER PUBLICATIONS

Database EMBL 'en ligne! CE 14392, accession No. U14392, Sep. 14, 1994 E.A Lockhart: "Cloning and sequencing of cerine GM–CSF", referred to as XP 0021488166.

McInnes, C.J. et al., "Cloning and expression of a cDNA encoding ovine granulocyte–macrophage colony–stimulating factor", Gene, 1991, vol. 105, No. 2, pp. 275–279.

Inumaru, S. et al., "cDNA cloning of porcine granulocyte–macrophage colony–stimulating factor", Immunology and Cell Biology, 1995, vol. 73, No. 5, pp. 474–476.

Sin, J., et al., "Protective immunity against heterologous challenge with encephalomyocarditis virus by VP1 DNA vaccination: effect of coinjection with a granulocyte–macrophage colony stimulating factor gene", Vaccine, 1997, vol. 15, No. 17/18 pp. 1827–1833.

Hartikka, J., et al., "An improved Plasmid DNA Expression Vector for Direct Injection into Skeletal Muscle", Human Gene Therapy, 1996, vol. 7, No. 10 pp. 1205–1217.

* cited by examiner

*Primary Examiner*—Lorraine Spector
(74) *Attorney, Agent, or Firm*—Frommer Lawrence & Haug, LLP; William S. Frommer; Thomas J. Kowalski

(57) ABSTRACT

The invention relates to the equine GM-CSF, its nucleotide coding sequence and its amino acid sequence, as well as its use as adjuvant in equine vaccination and as non-specific immunity stimulant. The invention also includes compositions containing equine GM-CSF or vectors expressing GM-CSF in vivo.

24 Claims, 2 Drawing Sheets

FIG. 1

Sequence of the equine GM-CSF gene

Figure 2:
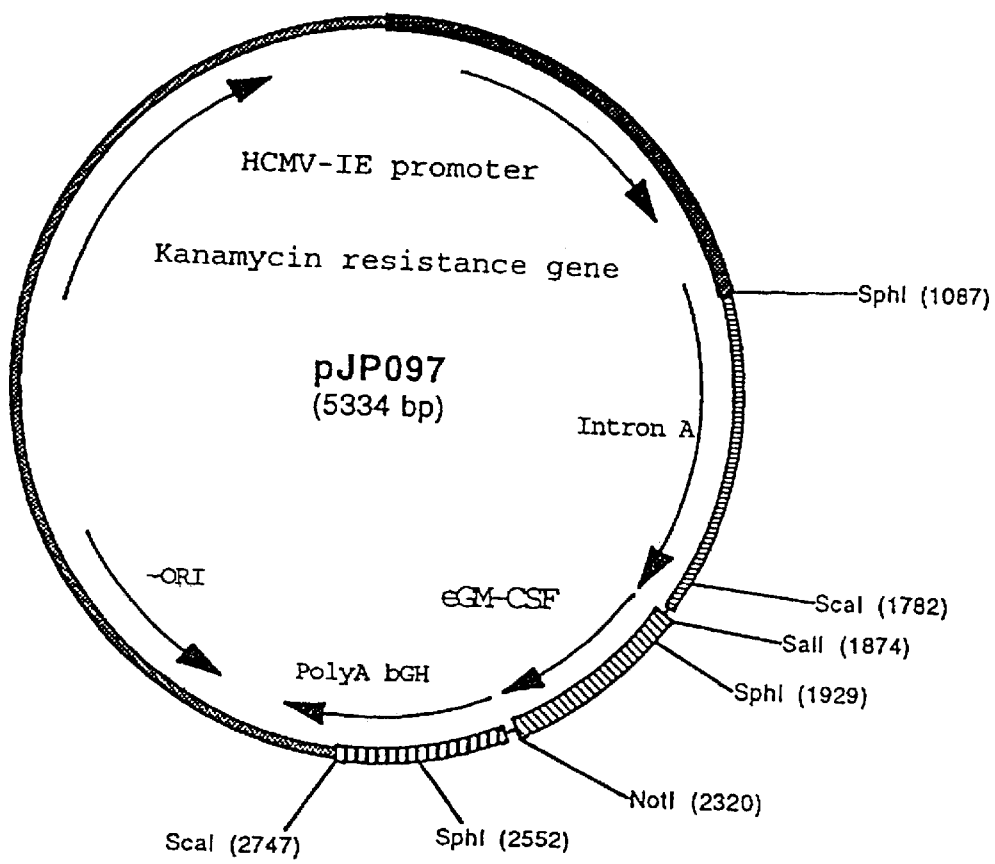

```
  1 ATG TGG CTG CAG AAC CTG CTT CTT CTG GGC ACT GTG GTT TAC AGC ATG CCC GCA CCC ACC
    TAC ACC GAC GTC TTG GAC GAA GAA GAC CCG TGA CAC CAA ATG TCG TAC GGG CGT GGG TGG
  1▶ M   W   L   Q   N   L   L   L   L   G   T   V   V   Y   S   M   P   A   P   T

61 CGC CAA CCC AGC CCT GTC ACT CGG CCC TGG CAG CAT GTG GAT GCC ATC AAG GAG GCC CTG
    GCG GTT GGG TCG GGA CAG TGA GCC GGG ACC GTC GTA CAC CTA CGG TAG TTC CTC CGG GAC
 21▶ R   Q   P   S   P   V   T   R   P   W   Q   H   V   D   A   I   K   E   A   L

121 AGC CTT CTG AAC AAC AGT AGT GAC ACT GCT GCT ATC ATG AAT GAA ACA GTA GAA GTC GTC
    TCG GAA GAC TTG TTG TCA TCA CTG TGA CGA CGA TAG TAC TTA CTT TGT CAT CTT CAG CAG
 41▶ S   L   L   N   N   S   S   D   T   A   A   I   M   N   E   T   V   E   V   V

181 TCT GAA ACG TTT GAC GCC GAG GAG CTG ACA TGC CTG CAG ACT CGC CTG AAG CTG TAC AAA
    AGA CTT TGC AAA CTG CGG CTC CTC GAC TGT ACG GAC GTC TGA GCG GAC TTC GAC ATG TTT
 61▶ S   E   T   F   D   A   E   E   L   T   C   L   Q   T   R   L   K   L   Y   K

241 CAG GGC TTG CGG GGC AGC CTC ATC AAG CTC GAA GGC CCC TTG ACC ATG ATG GCC AGC CAC
    GTC CCG AAC GCC CCG TCG GAG TAG TTC GAG CTT CCG GGG AAC TGG TAC TAC CGG TCG GTG
 81▶ Q   G   L   R   G   S   L   I   K   L   E   G   P   L   T   M   M   A   S   H

301 TAC AAG CAG CAC TGC CCC CCC ACC CTG GAA ACT TCC TGT GCA ACC CAG ATG ATC ACC TTC
    ATG TTC GTC GTG ACG GGG GGG TGG GAC CTT TGA AGG ACA CGT TGG GTC TAC TAG TGG AAG
101▶ Y   K   Q   H   C   P   P   T   L   E   T   S   C   A   T   Q   M   I   T   F

361 AAA AGT TTC AAA AAG AAC CTG AAG GAT TTT CTG TTT GAG ATC CCG TTT GAC TGC TGG AAG
    TTT TCA AAG TTT TTC TTG GAC TTC CTA AAA GAC AAA CTC TAG GGC AAA CTG ACG ACC TTC
121▶ K   S   F   K   K   N   L   K   D   F   L   F   E   I   P   F   D   C   W   K

421 CCA GCC CAG AAG TAA
    GGT CGG GTC TTC ATT
141▶ P   A   Q   K
```

Restriction map of the plasmid pJP097

SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (13)..(13)
<223> OTHER INFORMATION: nucleotide "y" can be either of the pyrimidine
      nucleotides "c" or "t"

<400> SEQUENCE: 1
tgggcactgt ggyctgcagc                                              20

<210> SEQ ID NO 2
<211> LENGTH: 17
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (9)..(9)
<223> OTHER INFORMATION: nucleotide "r" can be either of the purine
      nucleotides "a" or "g"

<400> SEQUENCE: 2
agcatgtgra tgccatc                                                 17

<210> SEQ ID NO 3
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 3
agctcccagg gctagctcct a                                            21

<210> SEQ ID NO 4
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 4
ccctgtttgt acagcttcag g                                            21

<210> SEQ ID NO 5
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 5
tgttgttcag aaggctcagg g                                            21

<210> SEQ ID NO 6
<211> LENGTH: 44
<212> TYPE: DNA
<213> ORGANISM: Artificial Sequence
<220> FEATURE:
<223> OTHER INFORMATION: oligonucleotide primer

<400> SEQUENCE: 6
catcatcatg tcgacgccac catgtggctg cagaacctgc ttct                44

<210> SEQ ID NO 7
<211> LENGTH: 41
<212> TYPE: DNA
<213> ORGANISM: Artificial Sequence
<220> FEATURE:
<223> OTHER INFORMATION: oligonucleotide primer

<400> SEQUENCE: 7
catcatcatg cggccgctac ttctgggctg ctggcttcca g                  41

<210> SEQ ID NO 8
<211> LENGTH: 435
<212> TYPE: DNA
<213> ORGANISM: Equine sp.
<220> FEATURE:
<221> NAME/KEY: CDS
<222> LOCATION: (1)..(432)
<223> OTHER INFORMATION: coding sequence of equine GM-CSF gene

<400> SEQUENCE: 8

```
atg tgg ctg cag aac ctg ctt ctt ctg ggc act gtg gtt tac agc atg         48
Met Trp Leu Gln Asn Leu Leu Leu Leu Gly Thr Val Val Tyr Ser Met
1               5                   10                  15 ccc gca ccc acc cgc caa ccc agc cct gtc act cgg ccc tgg cag cat         96
Pro Ala Pro Thr Arg Gln Pro Ser Pro Val Thr Arg Pro Trp Gln His
            20                  25                  30 gtg gat gcc atc aag gag gcc ctg agc ctt ctg aac aac agt agt gac        144
Val Asp Ala Ile Lys Glu Ala Leu Ser Leu Leu Asn Asn Ser Ser Asp
        35                  40                  45 act gct gct atc atg aat gaa aca gta gaa gtc gtc tct gaa acg ttt        192
Thr Ala Ala Ile Met Asn Glu Thr Val Glu Val Val Ser Glu Thr Phe
    50                  55                  60 gac gcc gag gag ctg aca tgc ctg cag act cgc ctg aag ctg tac aaa        240
Asp Ala Glu Glu Leu Thr Cys Leu Gln Thr Arg Leu Lys Leu Tyr Lys
65                  70                  75                  80 cag ggc ttg cgg ggc agc ctc atc aag ctc gaa ggc ccc ttg acc atg        288
Gln Gly Leu Arg Gly Ser Leu Ile Lys Leu Glu Gly Pro Leu Thr Met
                85                  90                  95 atg gcc agc cac tac aag cag cac tgc ccc ccc acc ctg gaa act tcc        336
Met Ala Ser His Tyr Lys Gln His Cys Pro Pro Thr Leu Glu Thr Ser
            100                 105                 110 tgt gca acc cag atg atc acc ttc aaa agt ttc aaa aag aac ctg aag        384
Cys Ala Thr Gln Met Ile Thr Phe Lys Ser Phe Lys Lys Asn Leu Lys
        115                 120                 125 gat ttt ctg ttt gag atc ccg ttt gac tgc tgg aag cca gcc cag aag        432
Asp Phe Leu Phe Glu Ile Pro Phe Asp Cys Trp Lys Pro Ala Gln Lys
    130                 135                 140 taa                                                                    435
```

<210> SEQ ID NO 9
<211> LENGTH: 144
<212> TYPE: PRT
<213> ORGANISM: Equine sp.

<400> SEQUENCE: 9

```
Met Trp Leu Gln Asn Leu Leu Leu Leu Gly Thr Val Val Tyr Ser Met
1               5                   10                  15

Pro Ala Pro Thr Arg Gln Pro Ser Pro Val Thr Arg Pro Trp Gln His
```

-continued

```
                    20                  25                  30
Val Asp Ala Ile Lys Glu Ala Leu Ser Leu Leu Asn Asn Ser Ser Asp
        35                  40                  45
Thr Ala Ala Ile Met Asn Glu Thr Val Glu Val Val Ser Glu Thr Phe
        50                  55                  60
Asp Ala Glu Glu Leu Thr Cys Leu Gln Thr Arg Leu Lys Leu Tyr Lys
65                      70                  75                  80
Gln Gly Leu Arg Gly Ser Leu Ile Lys Leu Glu Gly Pro Leu Thr Met
                85                  90                  95
Met Ala Ser His Tyr Lys Gln His Cys Pro Pro Thr Leu Glu Thr Ser
                100                 105                 110
Cys Ala Thr Gln Met Ile Thr Phe Lys Ser Phe Lys Lys Asn Leu Lys
        115                 120                 125
Asp Phe Leu Phe Glu Ile Pro Phe Asp Cys Trp Lys Pro Ala Gln Lys
        130                 135                 140
```

NUCLEIC ACIDS ENCODINGS EQUINE GM-CSF

This application is based upon and claims priority from U.S. Provisional application Serial No. 60/138,843, filed Jun. 10, 1999, U.S. Serial No. 60/138,843, and all documents cited therein, and all documents in documents cited in U.S. Serial No. 60/138,843, are hereby incorporated by reference.

The present invention relates to the nucleotide sequence of the gene encoding the horse cytokine GM-CSF, to expression vectors containing it, and to its use as adjuvant in equine vaccination and as nonspecific immunity stimulant.

The documents cited here are incorporated by reference into the present application. (All documents cited herein, and all documents cited in documents cited herein are hereby incorporated herein by reference).

The first discovery of a granulocyte-macrophage colony-stimulating factor (GM-CSF) dates from 1977 (Burgess A.W. et al. J. Biol. Chem. 1977, 252, 1998–2003). It is the murine GM-CSF, purified from mouse lung culture supernatants.

The biological activities of GM-CSF have been demonstrated by the work carried out on the murine and human GM-CSFs (Clark S. C. et al. Science 1987, 230, 1229; Grant S. M. et al. Drugs 1992, 53, 516).

GM-CSF has many physiological roles (Dy M. in "Les cytokines" Cavaillon J.-M., 1996, ed. Masson, Paris, France, 43–56). In particular, GM-CSF stimulates the production, the development and the formation of colonies of granulocytes, macrophages, eosinophils and megakaryocytes. GM-CSF induces in particular a macrophagic cytotoxocity, stimulates antibody-dependent cytotoxic activity (ADCC) and the recruitment of leukocytes at the level of the sites of inflammation.

The GM-CSFs from various animal species have already been identified.

The sizes of the nucleotide sequences encoding the known GM-CSFs from various species vary from 381 to 432 nucleotides. The human and murine nucleotide sequences have a degree of homology of 69%. The degree of homology is 54% at the level of the amino acid sequence (Cantrell M. A. et al. Proc. Natl. Acad. Sci. USA 1985, 82, 6250–6254). However, this homology does not allow any cross-activity between the two human and murine species (Metcalf D. et al. Blood 1986, 67, 37–45).

The administration of heterologous GM-CSF, that is to say obtained from a species other than the one treated, does not make it possible to obtain an optimum adjuvant effect, in particular a stimulation of the activity of the haematopoietic cells and a substantial increase in the immune response.

Up until now, it has not been possible to identify the equine GM-CSF. Yet this cytokine is of great interest for therapeutic and vaccinal applications for use in horses.

The applicant has succeeded in isolating and sequencing the equine GM-CSF gene. This gene was isolated after polymerase chain reaction (PCR) with the aid of the oligonucleotides described in the examples.

The equine GM-CSF gene has a size of 432 nucleotides (SEQ ID No. 8 and FIG. 1) and encodes a protein of 144 amino acids (SEQ ID No. 9 and FIG. 1). The protein encoded by this gene exhibits a homology of at least 75% with the GM-CSF polypeptide sequences of other animal species.

The subject of the present invention is therefore an isolated DNA fragment encoding equine GM-CSF, e.g. a fragment comprising SEQ ID No. 8. Its subject is also the DNA fragment having or consisting essentially of this sequence.

The subject of the present invention is also an isolated DNA fragment encoding the amino acid sequence SEQ ID No. 9.

The invention covers the equivalent nucleotide sequences of equine or synthetic origin, that is to say the nucleotide sequences encoding a protein of equivalent functionality and specificity in horses. The nucleotide sequences which differ by the degeneracy of the genetic code will of course be included. In particular, DNA sequences having an homology equal or greater than 90%, particularly than 92%, preferably than 95% with SEQ ID No. 8, are equivalent sequences.

An object is also DNA fragments comprising such a nucleotide sequence encoding the equine GM-CSF, e.g. according to SEQ ID No. 8 or a sequence encoding the amino acid sequence SEQ ID No. 9, this nucleotide sequence being associated, in the form of a fusion, with the nucleotide sequence encoding at least one immunogen or at least one immunogenically active fragment or at least one epitope of an immunogen. The DNA fragment then does not comprise a stop codon between the sequence encoding GM-CSF and the associated immunogen encoding sequence. For instance, referring to SEQ ID No. 8, the coding sequence inserted ends at nucleotide 432, and does not include the stop codon.

The subject of the present invention is also the isolated equine GM-CSF protein or polypeptide, e.g. that encoded by the nucleotide sequence SEQ ID No. 8 or by the equivalent of the latter as defined above.

The subject of the present invention is also the equine GM-CSF protein having the amino acid sequence SEQ ID No. 9.

The equine GM-CSF protein has a size of 144 amino acids. However, the present invention also comprises the proteins, protein fragments and polypeptides of equine origin or which are synthetic, having a size greater or equal than or less than these 144 amino acids, as well as the recombinant proteins (having one or more substitutions, deletions or additions) and the fusion proteins, as long as their biological activity (for the part which is common to GM-CSF) is substantially equivalent to that of the natural equine GM-CSF protein in vivo in horses and their species-specificity is not modified. Are encompassed as equivalents any of the amino acid sequences encoded by any of the equivalent nucleotide sequences as defined above.

The subject of the present invention is also a pure preparation of equine GM-CSF protein.

The subject of the present invention is also the expression vectors containing, as insert, any of the above defined DNA fragments or nucleotide sequences, in particular the equine GM-CSF gene (SEQ ID No. 8) or an equivalent thereof as defined above, as well as any of the nucleotide sequences encoding any of the above defined amino acid sequences. Also, the vector may further comprise a nucleotide sequence encoding at least one immunogen or at least one immunogenically active fragment or at least one epitope of an immunogen, which can be or not associated under the form of a fusion as described above.

The nucleotide sequence may be inserted into conventional in vitro expression systems of viral origin, such as Baculovirus, in particular propagated on insect cells, or cells of prokaryotic origin (for example *Escherichia coli*) or eukaryotic origin, in particular yeasts, especially *Saccharomiyces cerevisiae*, mammalian eukaryotic cells, especially hamster cells (for example hamster ovary cells or CHO) and horse cells. The invention therefore also covers expression systems transformed by a sequence according to the invention, the equine GM-CSF proteins thus produced and their use as adjuvant for vaccine and nonspecific immunity stimulant.

Preferably, the sequence according to the invention is introduced into in vivo expression vectors under conditions allowing the expression, in horses, of a functional equine GM-CSF protein, and possibly a nucleotide sequence encoding at least one immunogen or at least one immunogenically active fragment or at least one epitope of an immunogen. These expression vectors may be plasmids, viral vectors, such as poxviruses, for example the vaccinia virus, avipoxviruses (canarypox, fowlpox), including the species-specific poxviruses (swinepox, raccoonpox and camelpox), adenoviruses and herpesviruses, such as the equine herpesviruses.

The term plasmid is intended to cover any DNA transcription unit in the form of a polynucleotide sequence comprising the sequence of the equine GM-CSF gene and the elements necessary for its expression in vivo. The circular plasmid form, supercoiled or otherwise, is preferred. The linear form also falls within the scope of this invention.

Each plasmid comprises a promoter capable of ensuring, in the host cells, the expression of the gene inserted under its control. It is in general a strong eukaryotic promoter and in particular a cytomegalovirus early promoter CMV-IE, of human or murine origin, or optionally of other origin such as rat or guinea pig. More generally, the promoter is either of viral origin or of cellular origin. As a viral promoter other than CMV-IE, there may be mentioned the SV40 virus early or late promoter or the Rous Sarcoma virus LTR promoter. It may also be a promoter from the virus from which the gene is derived, for example the promoter specific to the gene. As cellular promoter, there may be mentioned the promoter of a cytoskeleton gene, such as for example the desmin promoter, or alternatively the actin promoter. When several genes are present in the same plasmid, they may be provided in the same transcription unit or in two different units.

The plasmids may also comprise other transcription regulating elements such as, for example, stabilizing sequences of the intron type, preferably intron II of the rabbit bêta-globin gene (van Ooyen et al. Science, 1979, 206: 337–344), signal sequence of the protein encoded by the tissue plasminogen activator gene (tPA; Montgomery et al. Cell. Mol. Biol. 1997, 43: 285–292), and the polyadenylation signal (polyA), in particular of the bovine growth hormone (bGH) gene (U.S. Pat. No. 5,122,458) or of the rabbit beta-globin gene.

The invention also covers the immunogenic compositions and the vaccines comprising the equine GM-CSF protein according to the invention, and at least one immunogenic or vaccinal preparation of equine pathogen, and a veterinarily acceptable excipient or vehicle. The notion of immunogenic preparation covers here any preparation capable, once administered to horses, of inducing an immune response directed against the equine pathogen considered, a response which is increased by the presence of the GM-CSF protein. It is preferably a vaccinal preparation capable of inducing an effective protection or a degree of protection against this pathogen, a degree of protection which is increased here by the presence of the equine GM-CSF protein. The immunogenic and vaccinal preparations intended in the invention cover all the known types, such as inactivated, attenuated live, subunit and recombinant (using an in vivo expression vector, in particular of viral or plasmid origin). As was seen above, the GM-CSF protein may be added as such to the immunogenic or vaccinal preparation to form, in the presence of veterinarily acceptable excipient or vehicle, an immunogenic composition or a vaccine ready to be administered. It is also possible to envisage combining the GM-CSF protein with a prolonged-release system designed to gradually release the protein.

According to a more advantageous mode of the invention, it is however preferable to express the GM-CSF protein in vivo using an in vivo expression vector as described above. In this case, it is also preferable that the immunogenic or vaccinal preparation is also of the recombinant type, based on the use of an in vivo expression vector, of the same type or of a different type. It is also possible to envisage using the same in vivo expression vector, comprising and expressing at least one equine pathogen immunogen and the equine GM-CSF protein.

The advantages of the use of GM-CSF during vaccinations are in particular the reduction in the dose of immunogen or of vector or DNA used. Furthermore, in some animals which do not respond when administered with a customary vaccine, the use of GM-CSF allows the stimulation of the immune response and its increase up to a protective level.

The present invention therefore preferably covers the immunogenic compositions and the vaccines comprising:

an in vivo expression vector containing a nucleotide sequence encoding an equine GM-CSF under conditions allowing the expression, in horses, of a functional equine GM-CSF protein, at least one in vivo expression vector containing at least one nucleotide sequence encoding at least one equine immunogen, it being understood that this vector or some or all of these vectors (when there are several vectors encoding various immunogens) may also constitute the GM-CSF vector (say the vector comprises at least the GM-CSF sequence and an immunogene sequence), and a veterinarily acceptable vehicle or excipient.

According to a preferred mode of the invention, the invention covers the immunogenic compositions and the vaccines of the DNA type, comprising a plasmid encoding and expressing the equine GM-CSF according to the invention and at least one other plasmid encoding and expressing an equine immunogen or an immunologically active fragment derived therefrom. Examples of plasmid constructs which contain an equine immunogen and which can be used in the invention are given in patent application WO-A-9803198. The invention also covers the DNA vaccines comprising a plasmid encoding and expressing simultaneously the equine GM-CSF and at least one equine immunogen.

The invention covers all the equine pathogens. There may be mentioned more particularly equine herpesvirus type 1 or type 4 (and preferably the invention provides for combination of both types), equine influenza virus, tetanus, *Borrelia burgdorferi*, Eastern, Western and Venezuelan equine encephalites, rabies virus. For the subunit vaccines and the recombinant vaccines, the equine immunogens are preferably selected from the group comprising the glycoproteins gB, gC and gD of the equine herpesvirus type 1 or type 4, the haemagglutinin (HA) and the nucleoprotein (NP) of the equine influenza virus, the C subunit fragment of the tetanus toxin, the *Borrelia burgdorferi* OspA protein, the Eastern, Western and Venezuelan equine encephalites E2 and C genes, the rabies virus G gene.

The subject of the present invention is also nonspecific immunity stimulating compositions, that is to say which can be used as a general immunity stimulant in horses. These compositions are administered in the presence or in the absence of a declared pathology, in general independently of any vaccine, in order to reinforce the immune defenses in horses. These compositions comprise GM-CSF according to the invention, in all the forms described above, protein or recombinant, preferably recombinant (in vivo viral or plasmid expression vector), and a veterinarily acceptable excipient or vehicle. The characteristics of these vectors have already been described.

The nonspecific stimulating compositions and the immunogenic compositions and the vaccines according to the invention may also comprise one or more immunity adjuvants, in particular selected from those normally used in equine vaccination against the pathogens (valencies) considered. The stimulating compositions and the immunogenic compositions and conventional vaccines (inactivated, attenuated live, subunit) may thus comprise, as conventional adjuvant, compounds of the carbomer or aluminum hydroxide type, or may be formulated in the form of an oil-in-water emulsion. For the stimulating compositions and the immunogenic compositions and recombinant vaccines based on a viral expression vector, there may be mentioned the oil-in-water emulsions.

According to a preferred mode of the invention, for the stimulating compositions of the plasmid type and the immunogenic compositions and vaccines of the plasmid type, the plasmid encoding and expressing the equine GM-CSF, the plasmid encoding and expressing GM-CSF and at least one equine immunogen, as well as the mixtures of plasmids containing the latter and at least one plasmid encoding an equine immunogen, may be advantageously formulated in a novel fashion with a cationic lipid containing a quaternary ammonium salt, of formula:

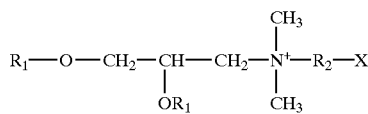

in which $R_1$ is a saturated or unsaturated linear aliphatic radical having 12 to 18 carbon atoms, $R_2$ is another aliphatic radical containing 2 or 3 carbon atoms, and X a hydroxyl or amine group It is preferably the DMRIE (N-(2-hydroxyethyl)-N,N-dimethyl-2,3-bis (tetradecyloxy)-1-propanammonium; WO-A-9634109), preferably coupled with a neutral lipid, DOPE (dioleoylphosphatidylethanolamine), to form preferably DMRIE-DOPE. Preferably, the recombinant vector mixture with this adjuvant is made immediately before use and preferably, before its administration to the animal, the mixture thus produced is allowed to form a complex, for example over a period ranging from 10 to 60 minutes, in particular of the order of 30 minutes.

When DOPE is present, the DMRIE:DOPE molar ratio preferably ranges from 95:5 to 5:95, more particularly 1:1. The plasmid:DMRIE or DMRIE-DOPE adjuvant weight ratio may range in particular from 50:1 to 1:10, in particular from 10:1 to 1:5, preferably from 1:1 to 1:2.

According to another advantageous mode of the invention, for the stimulating compositions of the recombinant type and the immunogenic compositions and vaccines of the recombinant type (viral vector or plasmid), it is possible to use, as adjuvant, polymers of acrylic or methacrylic acid or copolymers of maleic anhydride and of alkenyl derivative. The polymers of acrylic or methacrylic acid crosslinked in particular with polyalkenyl ethers of sugars or of polyalcohols are preferred. These compounds are known by the term carbomer (Pharmeuropa vol. 8, No. 2, June 1996). Persons skilled in the art can also refer to U.S. Pat. No. 2,909,462 (incorporated by reference) describing such acrylic polymers crosslinked with a polyhydroxylated compound having at least 3 hydroxyl groups, preferably not more than 8, the hydrogen atoms of at least three hydroxyls being replaced with unsaturated aliphatic radicals having at least 2 carbon atoms. The preferred radicals are those containing 2 to 4 carbon atoms, e.g. vinyls, allyls and other ethylenically unsaturated groups. The unsaturated radicals may themselves contain other substituents, such as methyl. The products sold under the name Carbopol□ (BF Goodrich, Ohio, USA) are particularly appropriate. They are crosslinked with an allyl saccharose or with allylpentaerythritol. Among them, there may be mentioned Carbopol® 974P, 934P and 971P.

Among the copolymers of maleic anhydride and of an alkenyl derivative, the EMAs® (Monsanto) are preferred which are copolymers of maleic anhydride and ethylene, linear or crosslinked, for example crosslinked with divinyl ether. Reference may be made to J. Fields et al., Nature, 186: 778–780, Jun. 4, 1960 (incorporated by reference). From the point of view of their structure, the polymers of acrylic or methacrylic acid and the EMAs® preferably consist of basic units of the following formula:

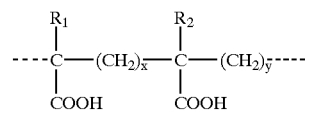

in which:
$R_1$ and $R_2$, which are identical or different, represent H or $CH_3$
x=0 or 1, preferably x=1
y=1 or 2, with x+y=2
For the EMAs®, x=0 and y=2. For the carbomers, x=y=1.

The dissolution of these polymers in water leads to an acidic solution which will be neutralized, preferably to physiological pH, to give the adjuvant solution into which the actual vaccine will be incorporated. The carboxyl groups of the polymer are then partly in COO⁻ form.

Preferably, a solution of carbomer or of EMA® is prepared in distilled water, preferably in the presence of sodium chloride, the solution obtained being at acidic pH. This stock solution is diluted by adding it to the required quantity (in order to obtain the desired final concentration), or a substantial part thereof, of water loaded with NaCl, preferably physiological saline (NaCl 9 g/l), in one or more portions with concomitant or subsequent neutralization (pH 7.3 to 7.4), preferably with NaOH. This solution at physiological pH will be used as it is to mix with the immunogenic or vaccinal preparation, in particular stored in lyophilized, liquid or frozen form.

The polymer concentration in the final vaccine composition will be 0.01% to 2% W/V, more particularly 0.06 to 1% W/V, preferably 0.1 to 0.6% W/V.

Another object of the invention is a method of immune stimulation and/or immunisation and/or vaccination of equine species, wherein a stimulating, immunogenic or vaccine composition according to the invention is administered to an animal from equine species, in particular a horse. Administration is preferably done via parenteral route, such as intramuscular, intradermal or sucutaneous route. One or more administrations can be done. In particular, in case of vaccination, administration is done each time the vaccine is administered.

The quantity of DNA used in the stimulating compositions and the immunogenic compositions and vaccines according to the present invention is between about 10 μg and about 2000 μg, and preferably between about 50 μg and about 1000 μg, for a given plasmid. Persons skilled in the art will have the competence necessary to precisely define the effective dose of DNA to be used for each therapeutic or vaccination protocol.

If a live vector is used, doses may be between $10^4$ and $10^{10}$ Pfu (plaque forming unit) preferably between $10^6$ and $10^8$ pfu.

For a composition containing GM-CSF protein, doses may be from 1 μg to 5 mg, preferably from 50 μg to 1 mg.

The dose volumes may be in particular between 0.5 and 5 ml, preferably between 2 and 3 ml.

The invention will now be described in greater detail with the aid of embodiments taken as nonlimiting examples and referring to the drawing in which:

FIG. 1: Sequences of the equine GM-CSF gene (SEQ ID No. 8) and protein (SEQ ID No. 9)

FIG. 2: Restriction map of the plasmid pJP097

SEQUENCE LISTING SEQ ID FOR THE CONSTRUCTS OF THE PRESENT INVENTION

SEQ ID No. 1 Oligonucleotide JP705

SEQ ID No. 2 Oligonucleotide JP706

SEQ ID No. 3 Oligonucleotide JP729

SEQ ID No. 4 Oligonucleotide JP730

SEQ ID No. 5 Oligonucleotide JP731

SEQ ID No. 6 Oligonucleotide JP734

SEQ ID No. 7 Oligonucleotide JP735

SEQ ID No. 8 Sequence of the equine GM-CSF gene (see FIG. 1)

SEQ ID No. 9 Sequence of the horse GM-CSF protein (see FIG. 1).

EXAMPLES

All the constructions of the plasmids were carried out using the standard molecular biology techniques (cloning, digestion with restriction enzymes, synthesis of a single-stranded complementary DNA, polymerase chain reaction, extension of an oligonucleotide with a DNA polymerase and the like) described by Sambrook J. et al. (Molecular Cloning: A Laboratory Manual. $2^{nd}$ Edition. Cold Spring Harbor Laboratory. Cold Spring Harbor. N.Y. 1989). All the restriction fragments used for the present invention, as well as the various polymerase chain reaction (PCR) fragments were isolated and purified using the "Geneclean®" kit (BIO101 Inc. La Jolla, Calif.).

Example 1

Preparation of the Total RNA of Horse Lymphocytes Stimulated In Vitro by Mitogens Horse blood was collected on a tube containing EDTA by taking blood from the jugular vein. The mononucleated cells were arrested by centrifugation on a Ficoll gradient and then cultured in a Petri dish 60 mm in diameter. The horse mononucleat d cells in culture were then stimulated either with concanavalin A (conA) (final concentration of about 5 μg/ml) or with phytohaemagglutinin (PHA) (final concentration of about 10 μg/ml). After stimulation, the "ConA" and "PHA" lymphoblasts were harvested by scraping the culture dishes, and the total RNA of these cells was extracted using the "mRNA isolation kit for white blood cells" (Boehringer Mannheim/Roche Cat # 1 934 325).

Example 2

Isolation of the Gene Encoding the Equine GM-CSF

The oligonucleotides JP075 and JP076 were synthesized and have the following sequences:

JP705 (SEQ ID No. 1) (20 mer)
5'TGGGCACTGTGGYCTGCAGC3'

JP706 (SEQ ID No. 2) (17 mer)
5'AGCATGTGRATGCCATC3'

These oligonucleotides were used with the 5'/3'RACE kit (Boehringer Mannheim/Roche Cat # 1 734 792) in order to generate the 3'RACE clones 6S4, 6W6 and 6W7. The 3' consensus sequence established from these 3 clones was used to synthesize the oligonucleotides JP729, JP730 and JP731 which will serve for the generation of the corresponding 5'RACE clones:

JP729 (SEQ ID No. 3) (21 mer)
5'AGCTCCCAGGGCTAGCTCCTA3'

JP730 (SEQ ID No. 4) (21 mer)
5'CCCTGTTTGTACAGCTTCAGG3'

JP731 (SEQ ID No. 5) (21 mer)
5'TGTTGTTCAGAAGGCTCAGGG3'

The corresponding 5'RACE clones obtained were the clones 7D2 and 7D10. The consensus sequences generated from the 3'RACE clones and the 5'RACE clones were used to amplify the entire sequence of the equine GM-CSF gene according to the reverse transcriptase technique followed by a PCR. The total RNA extracted from the horse lymphocytes stimulated by ConA or by PHA (Example 1) served as template for the complementary DNA first strand synthesis. This complementary DNA first strand was produced by extension of the oligonucleotide p(dT)15 (Boehringer Mannheim/Roche Cat # 814 270). The single stranded complementary DNA obtained was then used as template for a PCR reaction with the following oligonucleotides:

JP734 (SEQ ID No. 6) (44 mer)
5'CATCATCATGTCGACGCCACCATGTG-GCTGCAGAACCTGCTTCT3' and JP735 (SEQ ID No. 7) (41 mer)
5'CATCATCATGCGGCCGCTACT-TCTGGGCTGCTGGCTTCCAG3' in order to amplify a PCR fragment of about 500 base pairs (bp). This fragment was purified by agarose gel electrophoresis (=fragment A).

Example 3

Construction of the Plasmid pJP097 and Sequence of the Equine GM-CSF Gene

Fragment A (Example 2) was digested with NotI and SalI and the NotI-SalI fragment thus obtained was ligated into the plasmid pVR1012 (Hartikka J. et al. Human Gene Therapy, 1996, 7, 1205–1217), previously digested with NotI and SalI, to give the plasmid pJP097 (5334 bp, FIG. 2). The NotI-SalI fragment cloned into this plasmid was completely sequenced. This sequence (SEQ ID No. 8), which encodes a protein of 144 amino acids (SEQ ID No. 9) is the horse GM-CSF cytokine (=equine GM-CSF) represented in FIG. 1.

Example 4

Biological Activity In Vitro of the Product of the Equine GM-CSF Gene

CHO-K1 cells (hamster ovary cells, accessible from the strain depository American Type Culture Collection under the access number CCL-61) were cultured in minimum essential medium or MEM (Gibco-BRL) in Petri dishes 60 mm in diameter and transfected with 5 µg of plasmid pJP097, previously complexed with 10 Al of LipofectAmine PLUS® (Cat #10964-013, Gibco-BRL, Cleveland, Ohio, USA). The conditions for forming the DNA/LipofectAmine® complexes and for transfecting the cells were those recommended by the supplier (Gibco-BRL). 48 hours after the transfection, the culture supernatants are harvested and frozen.

Bone marrow cells collected from pigs are cultured in a semisolid Methocult medium (Cat #H4230 from StemCell Technologies). These cultures are then supplemented or otherwise (negative control) with 10 µl of the supernatant of the cells transfected with the plasmid pJP097. Two independent transfections were carried out with the plasmid pJP097, encoded pJP097 T1 and pJP097 T2. Each supernatant (10 µl diluted 1/10) is tested in parallel in 3 culture dishes. The negative control consists of a CHO culture supernatant. After 14 days of culture, the dishes are examined for the formation of colonies of macrophages, and the colonies which may be present are counted.

The supernatants of CHO cells transfected with the plasmid pJP097 gave the following results:

| Plasmid/dilution supernatant | No. of dishes | Mean number of colonies per dish | Standard deviation |
|---|---|---|---|
| Control | 3 | 0 | 0 |
| pJP097 T1 (eGM-CSF) | 3 | 12 | 2 |
| pJP097 T2 (eGM-CSF) | 3 | 15 | 0 |

These results show that the product of the equine GM-CSF gene expressed by the plasmid pJP097 has a GM-CSF-type activity on cells in vitro.

Example 5

Preparation of the Plasmids According to the Invention

For the preparation of the plasmids intended for the vaccination of horses, it is possible to use any technique allowing a suspension of purified plasmids to be obtained. These techniques are well known to persons skilled in the art. The production of the plasmids is carried out by culturing *Escherichia coli* K12 bacteria transformed with the plasmids according to the invention. There may be mentioned in particular the alkaline lysis technique followed by two successive ultracentrifugations on cesium chloride gradient in the presence of ethidium bromide as described in Sambrook J. et al. (Molecular Cloning: A Laboratory Manual. 2nd edition. Cold Spring Harbor Laboratory. Cold Spring Harbor. N.Y. 1989). Reference may also be made to patent applications WO-A-95/21250 and WO-A-96/02658 which describe methods for producing, on an industrial scale, plasmids which can be used for vaccination. For the purposes of vaccine production, the plasmids are resuspended so as to obtain solutions at high concentration (>2 mg/ml) which are compatible with storage. To do this, the plasmids are resuspended either in ultrapure water, or in TE buffer (10 mM Tris-HCl; 1 mM EDTA; pH 8.0).

Example 6

Manufacture of the Vaccines According to the Invention and Administration

The stock of plasmid pJP097 is diluted in TE buffer, in physiological saline or in PBS buffer, and mixed with various vaccinal plasmids expressing protective immunogens. These plasmids may be, for example, those cited in the examples of patent application PCT WO 98/03198.

The horses are vaccinated with doses of 100 µg, 250 µg or 500 µg per plasmid.

The various mixtures of "immunogenic" plasmids and of the plasmid pJP097 "equine GM-CSF" thus obtained are coadministered by the intramuscular route (syringe+needle) into the neck or breast muscles. In this case, the vaccinal doses are injected in a volume of 2 ml.

The intramuscular injections may also be carried out using a liquid jet injection apparatus (without needle) which drives a dose of e.g. 0.5 ml. If necessary, several successive administrations may be made in the same animal in order to inject volumes greater than 0.5 ml. The successive shots are then made apart, so that the areas for injection are separated by about 1 to 2 centimeters.

The injections may also be carried out by the intradermal route using a liquid jet injection apparatus (without needle) delivering a dose of 0.2 ml at 5 sites (0.04 ml per site of injection) (for example "PIGJET" Endoscoptic apparatus, Laon, France).

The horses are typically vaccinated using two injections of mixtures of plasmids according to the invention carried out with a 4–5 week's interval.

Example 7

Formulation of the Plasmids According to the Invention

The mixture of "immunogenic" plasmids and of the plasmid pJP097 is diluted in TE buffer, in physiological saline and in PBS buffer so as to obtain a concentration of 1 mg/ml. A solution of DMRIE-DOPE at 0.75 mM is prepared by taking up a lyophilisate of DMRIE-DOPE in a suitable volume of sterile $H_2O$.

The formation of plasmid DNA-lipid complexes is achieved by diluting, in equal parts, the 0.75 mM DMRIE-DOPE solution with the DNA solution at 1 mg/ml. The DNA solution is gradually introduced, with the aid of a seamed 26G needle, along the wall of the vial containing the cationic lipid solution so as to avoid the formation of foam. Gentle shaking is carried out as soon as the two solutions have been mixed. A composition comprising 0.375 mM DMRIE-DOPE and 500 µg/ml of DNA is finally obtained.

It is desirable for all the solutions used to be at room temperature for all the operations described above. The DNA/DMRIE-DOPE complex formation is allowed to take place at room temperature for 30 minutes before immunizing the animals as described in Example 6.

It should be clearly understood that the invention defined by the appended claims is not limited to the specific embodiments indicated in the description above, but encompasses the variants which depart from neither the scope nor the spirit of the present invention.

What is claimed is:

1. An isolated DNA molecule comprising a nucleotide sequence as set forth in SEQ ID No. 8.

2. An isolated DNA molecule according to claim 1, further comprising a nucleotide sequence encoding at least one immunogen or at least one immunologically active fragment of an immunogen.

3. The isolated DNA molecule of claim 2 wherein the immunogen is an immunogen of an equine pathogen.

4. An isolated DNA molecule according to claim 1, further comprising a nucleotide sequence encoding at least one immunogen of an equine pathogen or at least one inmmunologically active fragment of an immunogen of an equine immunogen.

5. An isolated fusion protein encoded by the isolated DNA molecule fragment according to claim 2 or 4.

6. An isolated DNA molecule encoding an amino acid sequence as set forth in SEQ ID No. 9.

7. An isolated DNA molecule consisting of a nucleotide sequence as set forth in SEQ ID No. 8.

8. A vector that contains the isolated DNA molecule according to any one of claims 1, 2, 4, 6 or 7.

9. An isolated cell containing the vector of claim 8.

10. The vector of claim 8 that expresses the isolated DNA molecule under appropriate conditions.

11. A method for producing an isolated equine GM-CSF polypeptide or an isolated fusion protein comprising transforming or transfecting a cell with the vector of claim 10, and growing the cell under conditions which result in expression of the protein encoded by said DNA.

12. An isolated cell containing the vector of claim 10.

13. The vector of claim 10 wherein the vector expresses the isolated DNA molecule in vitro under appropriate conditions.

14. An isolated cell containing the vector of claim 13.

15. An isolated DNA molecule having at least 90% sequence identity to SEQ ID NO:8 and encoding equine GM-CSF.

16. An isolated DNA molecule having at least 92% sequence identity to SEQ ID NO:8 and encoding equine GM-CSF.

17. An isolated DNA molecule having at least 95% sequence identity to SEQ ID NO:8 and encoding equine GM-CSF.

18. The isolated DNA molecule according to any one of claims 15–17, further comprising a nucleotide sequence encoding at least one immunogen or at least one immunologically active fragment of an immunogen.

19. An isolated fusion protein encoded by the isolated DNA molecule according to claim 18.

20. A vector that contains the isolated DNA molecule according to claim 18.

21. The isolated DNA molecule according to any one of claims 15–17, further comprising a nucleotide sequence encoding at least one immunogen of an equine pathogen or at least one immunologically active fragment of an immunogen of an equine immunogen.

22. An isolated fusion protein encoded by the isolated DNA molecule according to claim 21.

23. A vector that contains the isolated DNA molecule according to claim 21.

24. A vector that contains the isolated DNA molecule according to any one of claims 15–17.

* * * * *

UNITED STATES PATENT AND TRADEMARK OFFICE
CERTIFICATE OF CORRECTION

PATENT NO.    : 6,645,740 B1
DATED         : November 11, 2003
INVENTOR(S)   : Michel Bublot et al.

It is certified that error appears in the above-identified patent and that said Letters Patent is hereby corrected as shown below:

<u>Title page,</u>
Item [73], Assignee:, change "Merial Limited, London (GB); Merial LLC, Duluth, GA (US)" to -- Merial Limited, Registered in England and Wales No.3332751, with Registered Office at P.O. Box 327, Sandringham House, Sandringham Avenue, Harlow Business Park, Harlow Essex CM 19 5TG, England, and domesticated in Delaware, USA as Merial LLC, with a place of business at 3239 Satellite Blvd., Duluth, GA 30096-4640 USA --

Signed and Sealed this

Sixth Day of April, 2004

JON W. DUDAS
*Acting Director of the United States Patent and Trademark Office*